(12) United States Patent
Arieli et al.

(10) Patent No.: US 9,696,134 B2
(45) Date of Patent: Jul. 4, 2017

(54) SYSTEM FOR PERFORMING DUAL PATH, TWO-DIMENSIONAL OPTICAL COHERENCE TOMOGRAPHY (OCT)

(71) Applicant: ADOM, ADVANCED OPTICAL TECHNOLOGIES LTD., Lod (IL)

(72) Inventors: Yoel Arieli, Jerusalem (IL); Yosef Weitzman, Tel Aviv (IL)

(73) Assignee: ADOM, ADVANCED OPTICAL TECHNOLOGIES LTD., Lod (IL)

( * ) Notice: Subject to any disclaimer, the term of this patent is extended or adjusted under 35 U.S.C. 154(b) by 74 days.

(21) Appl. No.: 14/417,971

(22) PCT Filed: Jul. 28, 2013

(86) PCT No.: PCT/IL2013/050641
§ 371 (c)(1),
(2) Date: Jan. 28, 2015

(87) PCT Pub. No.: WO2014/020597
PCT Pub. Date: Feb. 6, 2014

(65) Prior Publication Data
US 2015/0168125 A1    Jun. 18, 2015

(30) Foreign Application Priority Data
Jul. 30, 2012    (IL) .......................................... 221187

(51) Int. Cl.
*A61B 3/10*   (2006.01)
*G01B 9/02*   (2006.01)

(52) U.S. Cl.
CPC ............ *G01B 9/0203* (2013.01); *A61B 3/102* (2013.01); *G01B 9/02032* (2013.01);
(Continued)

(58) Field of Classification Search
USPC ........................................................ 351/211
See application file for complete search history.

(56) References Cited

U.S. PATENT DOCUMENTS

| | | |
|---|---|---|
| 2005/0254059 A1 | 11/2005 | Alphonse |
| 2009/0168017 A1 | 7/2009 | O'Hara et al. |

(Continued)

FOREIGN PATENT DOCUMENTS

| | | |
|---|---|---|
| EP | 2243420 A1 | 10/2010 |
| GB | 2485274 A | 5/2012 |

(Continued)

OTHER PUBLICATIONS

International PCT Search Report, PCT/IL2013/050641, 15 Pages, Date of Mailing Dec. 23, 2013.
(Continued)

*Primary Examiner* — Jack Dinh
(74) *Attorney, Agent, or Firm* — Moser Taboada

(57) ABSTRACT

A system (10) for measuring a physical characteristic of an object (11) using dual path, two-dimensional Optical Coherence Tomography (OCT) includes an extended broadband light source (13) producing an incident light beam (14) and an interferometer (15) having a beam splitter (16) that splits the incident beam into first and second component (17, 18) beams and directs the second component beam (18) on to a moveable mirror (19) for creating an optical path difference between the first component beam (17) and a reflection (20) of the second component beam. A focusing lens (21) having a focal plane (22) focuses the first component beam and the reflection of the second component beam to form a fringe pattern (23) on the focal plane, and a configurable imaging system (25) images the fringe pattern on to a plane (12) of the object to allow two-dimensional measurement of the object without spatial scanning.

18 Claims, 5 Drawing Sheets

(52) U.S. Cl.
CPC ..... *G01B 9/02036* (2013.01); *G01B 9/02043* (2013.01); *G01B 9/02044* (2013.01); *G01B 9/02057* (2013.01); *G01B 9/02065* (2013.01); *G01B 9/02091* (2013.01); *G01B 2290/60* (2013.01)

(56) References Cited

U.S. PATENT DOCUMENTS

| | | |
|---|---|---|
| 2009/0262360 A1 | 10/2009 | Bille et al. |
| 2010/0056928 A1 | 3/2010 | Zuzak et al. |
| 2011/0022328 A1 | 1/2011 | Granot et al. |
| 2011/0298896 A1 | 12/2011 | Dillon et al. |
| 2012/0013908 A1 | 1/2012 | Galle |
| 2012/0116703 A1 | 5/2012 | Pavillon et al. |
| 2012/0271176 A1 | 10/2012 | Moghaddam et al. |

FOREIGN PATENT DOCUMENTS

| | | |
|---|---|---|
| WO | WO-2009058850 A1 | 5/2009 |
| WO | WO-2012035148 A1 | 3/2012 |
| WO | WO-2012035170 A1 | 3/2012 |

OTHER PUBLICATIONS

Oh et al., "Spectrally-Modulated Full-Field Optical Coherence Microscopy for Ultrahigh-Resolution Endoscopic Imaging", Optics Express, Optical Society of America, vol. 18, Issue 19, pp. 8675-8684, Sep. 18, 2006.

Subhash, "Full-Field and Single-Shot Full-Field Optical Coherence Tomography: A Novel Technique for Biomedical Imaging Applications", Advances in Optical Technologies, vol. 1315, Issue 3, pp. 26, Jan. 1, 2012.

Extended European Search Report dated Jun. 1, 2016 for Application No. 13826457.7.

Oh et al., "Spectrally-Modulated Full-Field Optical Coherence Microscopy for Ultrahigh-Resolution Endoscopic imaging", Optics Express, OSA (Optical Society of America), US, vol. 14, Issue 19, pp. 8675-8684, Sep. 18, 2006.

Subhash et al., "Full-Field and Single-Shot Full-Field Optical Coherence Tomography: A Novel Technique for Biomedical Imaging Applications", Advances in Optical Technologies, vol. 1315, Issue 3, pp. 205-226, Jan. 1, 2012.

Extended European Search Report mailed Jun. 1, 2016 for Application No. 13826457.7.

SYSTEM FOR PERFORMING DUAL PATH, TWO-DIMENSIONAL OPTICAL COHERENCE TOMOGRAPHY (OCT)

FIELD OF THE INVENTION

The present invention relates to surface optical measurements, and more particularly, to a method and apparatus for measuring the surface and layers of an object.

BACKGROUND OF THE INVENTION

Optical Coherence Tomography (OCT) is a technique for obtaining sub-surface images of translucent or opaque materials at a resolution equivalent to a low-power microscope. It is effectively 'optical ultrasound', imaging reflections from within tissue to provide cross-sectional images. It is known to use Optical Coherence Tomography (OCT) for taking cross-sectional pictures of the retina in order to diagnose and follow treatment in certain eye conditions and diseases.

Light in an OCT system is broken into two arms—a sample arm (containing the item of interest) and a reference arm (usually a mirror). The combination of reflected light from the sample arm and reference light from the reference arm gives rise to an interference pattern, but only if light from both arms have an optical difference of less than a coherence length. By scanning the mirror in the reference arm, a reflectivity profile of the sample can be obtained (this is time domain OCT). Areas of the sample that reflect back a lot of light will create greater interference than areas that do not. Any light that is outside the short coherence length will not interfere. This reflectivity profile, called an A-scan, contains information about the spatial dimensions and location of structures within the item of interest. A cross-sectional tomograph (B-scan) may be achieved by laterally combining a series of these axial depth scans (A-scan).

WO 2006/103663 discloses a method and apparatus for analyzing optical properties of an object using a light beam having a plurality of amplitudes, phases and polarizations of a plurality of wavelengths impinging from the object, obtaining modified illuminations corresponding to the light beam, modulating the light beam, analyzing the modulated light beam, and obtaining a plurality of amplitudes, phases and polarizations maps of the plurality of wavelengths, which are used to determine the object's optical properties.

The use of OCT for modulating the light before it strikes the object is described, for example, in WO 2008/087613, which discloses an apparatus and method combining achromatic complex Fourier domain OCT signal reconstruction with a common path and dual beam configuration. Light is directed through an interferometer, which splits the light to a dual beam and directs the two beams to the object in a common path. The combined dual beam interacts with a multi-layered object to obtain tomograms of a single point of the object. A B scan is required.

U.S. Pat. No. 7,281,801 describes a system and method for measuring the thickness of a tear film layer and the heights of tear menisci around upper and lower eyelids of an eye. A plurality of images are acquired between consecutive blinks the eye using optical coherence tomography (OCT). The images depict the tear film layer and tear menisci as distinct from the cornea of the eye. In an embodiment, a plurality of reflectivity profiles from an OCT image are aligned and averaged. The difference between a first peak and a second peak of the average reflectivity profile is measured to determine the thickness of the tear film layer. A B scan is required.

Alex Zlotnik et al. "*Full Field Spectral Domain Optical Coherence Tomography with Improved Extended Depth of Focus*", OSA/CLEO/QELS 2010 discloses the use of an extended light source by creating interference fringes at the focal plane of a lens. An interfering phase mask is used to extend the depth of focus.

Drexler et al. "*Dual Beam Optical Coherence Tomography*" in Signal Identification for Ophthalmologic Diagnosis directs reference and object beams to the object. The light that is reflected back by the cornea serves as a reference for the light reflected by the retina. This requires a B scan and requires a sensor having very high spectral resolution owing to the high optical path difference between the reference beam and the object beam.

WO/2008/087613 discloses an apparatus and a method combining achromatic complex Fourier Domain OCT signal reconstruction with a common path and dual beam configuration. The apparatus directs a modulated interferometric point light source to an object to be measured and is not able to measure optical characteristics of a two-dimensional object within an optical system other than by point-by-point scanning.

US 2009/0080739 discloses a similar approach for performing spectral OCT imaging on a target by repeatedly scanning the target along a transverse scanning line with an object beam derived from an OCT interferometer having a narrowband source. The wavelength of the narrowband source is modulated over a range of wavelengths at a rate that is slow relative to the rate of scanning the target. The object beam returned from the target is detected to produce a set of data obtained from multiple scans along said scanning line over the entire range of wavelengths. The data is then processed to extract an OCT image (typically a B-scan) of the target containing depth information.

The above-referenced publications are representative of those that use OCT to image successive points of an object and thus require scanning of the OCT beam over a complete area of interest. OCT systems of this type involve the use of short coherent light, that is, light with a distinct spectral width and therefore short time coherence. The object is scanned point by point along a line extending on the object surface in the x-direction by the measurement beam of an interferometer. Under every surface point the measurement beam also penetrates into the object (in the z-direction) and the diffusely reflected light is interfered with the reference beam of the interferometer. Interference occurs because of the use of short coherence light only when the measurement beam and reference beam have the same path length within the coherence length.

The literature recognizes the deficiency of such an approach and addresses the need to perform area imaging. Thus, for example, U.S. Pat. No. 7,695,140 (Fercher) describes an ophthalmologic measuring method that can depict three-dimensional structures of the interfaces of an eye by means of low coherence interferometry based on reference points. To this end, the pupil is illuminated at a number of points by a low coherence light source. The measurement radiation reflected at these points by the interfaces and surfaces of the eye is superimposed with a reference radiation. The measurement data generated thereby are spectrally split up by a diffraction grating, projected onto a two-dimensional detector array, and routed to a control unit that determines a three-dimensional structure of all intraocular interfaces and surfaces of the eye. This makes it possible to determine the depth positions of the measuring beams at many pupil points with a single image taken by the array camera by illuminating the pupil with an aperture grid, and the reference mirror contains a periodic phase grid.

U.S. Pat. No. 6,810,140 discloses a system for three dimensional real-time imaging apparatus of the ocular retina, wherein laser rays are formed into a two dimensional ray surface sequentially with time by using a polygon mirror motor and galvanometer and irradiated on the almost transparent retina through the pupil. The optical system is complex and the polygon mirror performs optical scanning.

There is thus required a method and system that uses a dual beam and produces a two-dimensional area image without the need for scanning.

SUMMARY OF THE INVENTION

The invention describes a method and an apparatus having the features of the respective independent claims for performing optical measurements by using a common-path interferometer and a modulated light source.

In accordance with one aspect, a combination of a common-path interferometer and a modulated light source enables measuring an image of a 2D object created by an independent optical system without the need for a reference light beam. This has the advantage of enabling interference measurement of a 2D object without the need for matching the reference beam to the object beam.

According to one embodiment a dual path interferometer and spectral imaging system are combined for measuring a 2D object.

In accordance with another embodiment a common-path interferometer and spectral imaging system are combined for measuring an image of a 2D object created by an independent optical system without the need for a reference light beam.

In accordance with another embodiment a dual path interferometer and a spectrally modulated light source are combined to enable measurement a 2D object without the need for moving the interferometer's reference mirror.

In accordance with another embodiment a common path interferometer and a spectrally modulated light source are combined to enable measurement a 2D object without the need for a reference light beam.

In accordance with another embodiment a common path interferometer and a spectrally modulated light source are combined to enable measurement a 2D object without the need for a movable component in the interferometer.

In accordance with another embodiment a common-path interferometer and a spectrally modulated light source are combined to enable measurement an image of a 2D object created by an independent optical system without the need for a reference light beam and a movable component in the interferometer.

In accordance with another embodiment an imaging system and spectral imaging system are combined for measuring a 2D layered object without the need for a reference mirror.

In accordance with another embodiment of an imaging system and a spectrally modulated light source are combined to enable measurement a 2D layered object without the need for a reference mirror and without the need for spectrometer or spectral imaging system.

It is therefore a first object of the present invention to provide a method and system that performs dual path, two-dimensional Optical Coherence Tomography (OCT) on an object lying in a specific plane in order to measure a physical characteristic of the object by means of a two-dimensional area image that avoids the need for point-by-point scanning.

This object is realized in accordance with the invention by a system for performing dual path, two-dimensional Optical Coherence Tomography (OCT) on an object lying in a specific plane in order to measure a physical characteristic of the object, said system comprising:

an extended broadband light source for producing an incident light beam, a spatial light modulator (SLM) that modulates, in time, the spectrum of the light source differently in the spatial domain to obtain, in time, different fringe patterns.

The spatial light modulator (SLM) may consist of interferometers of any kind, tunable filters etc.

a configurable imaging system for imaging the fringe patterns on to said specific plane so as to allow two-dimensional measurement of the object without spatial scanning.

By "extended" is means that the light source is not a point light source and directs an incident beam over a large, i.e. extended area. Likewise, by "broadband" is meant that the light is not monochromatic. These two properties of the light source cooperate such that the components colors of the light source appear as colored fringes at the input to the imaging system.

Preferably, according to the invention the object is multilayered, one of whose serves as the reference layer thus avoiding the need for a reference beam. In the case of the eye, the reference layer may be constituted by one surface in the retina.

In one application of the invention the object whose physical characteristic is to be measured is an optical system having a lens upstream of the specific plane in the optical system where the object is located. More particularly, the optical system may be an eye whose lens is constituted by the combination of the cornea and the intra-ocular lens both of which act to refract incoming light. This has prevented use of two-dimensional OCT for measuring characteristics of the eye using the advantageous broadband light sources and interferometry without the need for point-by-point scanning. In general, measuring an object using interferometer requires that the reference arm and the object arm should be identical. If the object is located in an optical system, the reference arm should include an identical optical system and this cannot be attained in measuring Biological objects. However, in the invention, since the reference layer may be constituted by one surface in the retina, there is no need for the reference arm and the retina can be measured not point by point but in 2D at once.

This idea of avoiding the need for reference mirror and enabling measuring the retina in 2D at once rather than point by point, can be implemented using any kind of light source, such as broadband or monochromatic light source, extended or point light source, swept source etc. It can also implemented in point by point Time domain OCT or Fourier domain OCT.

In one embodiment of the invention, an extended broadband light source is modulated to produce interference fringes at the focal plane of a lens, which are then projected on to the object. This allows us to use an existing i.e. independent optical system to project the fringes on to the object.

The spectrum of the light source is modulated be means of moving one mirror of a Michelson interferometer.

By controlling the focal length of the projection system it is thus possible to control on which part of the object in 3D space we want to perform tomography.

Furthermore since the fringes are located at the effective focal plane of the lens after the interferometer and the illumination system is a separate unit, we therefore separate between the image plane of the light source and the image plane of the fringes produced by the light source.

The fringes at the focal plane of the lens will be of a different color pattern relative to out-of-focus fringes that are imaged in front of or behind the focal plane. So even without moving the interferometer's mirror in order to adjust the optical path difference (OPD), the colors and form of the fringes on the object may be used as an indication of depth.

The invention finds application not only to measure the different layers of the retina but by changing the focus of the projection system may be used to measure the intraocular lens or tear film.

BRIEF DESCRIPTION OF THE DRAWINGS

In order to understand the invention and to see how it may be carried out in practice, embodiments will now be described, by way of non-limiting example only, with reference to the accompanying drawing, in which:

FIG. 1b shows schematically a fringe pattern produced by the system of FIG. 1a;

DETAILED DESCRIPTION OF EMBODIMENTS

Figure 1A:
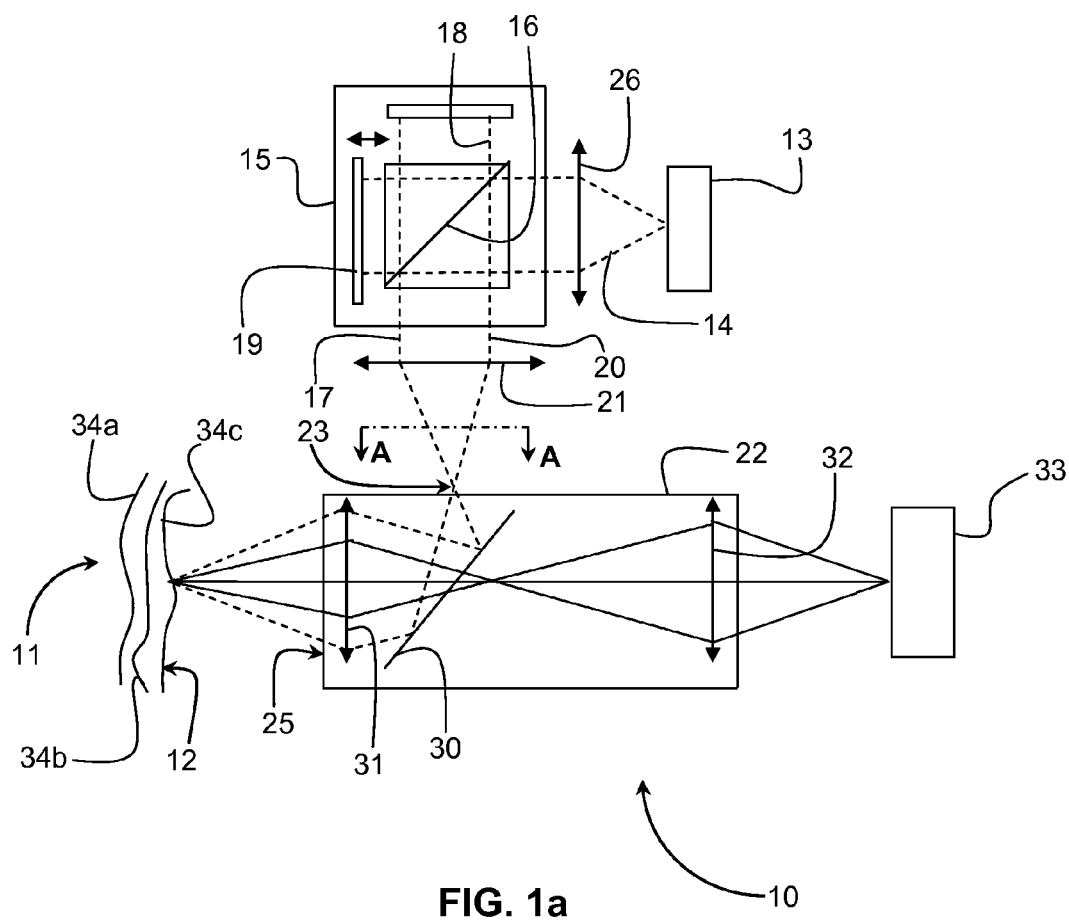
FIG. 1a is a schematic diagram of an optical system according to an embodiment of the invention.
Figure 1B:
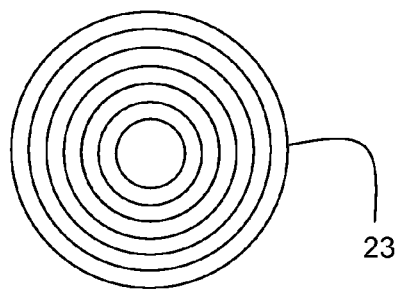

FIG. 1a shows schematically a system 10 for performing dual path, two-dimensional Optical Coherence Tomography (OCT) on an object 11 lying in a specific plane 12 in order to measure a physical characteristic of the object. The system 10 comprises an extended broadband light source 13 for producing an incident light beam 14 and a dual beam interferometer 15 for intercepting the incident light beam and directing it via a beam splitter 16 that splits the incident beam into first and second component beams 17 and 18, respectively. The interferometer 15 directs the second component beam 18 on to a moveable mirror 19 for creating an optical path difference between the first component beam 17 and a reflection 20 of the second component beam 18. A focusing lens 21 having a focal plane 22 is configured for focusing the first component beam 17 and the reflection 20 of the second component beam to form a fringe pattern 23 on the focal plane 22. The fringe pattern 23 comprises a series of concentric circles of different colors as shown schematically in FIG. 1b.

A configurable imaging system shown generally as 25 images the fringe pattern 23 on to the plane 12 so as to allow two-dimensional measurement of the object without spatial scanning. In some embodiments there may be included a second focusing lens 26 between the light source 13 and the interferometer 15 located relative to the light source so as to direct the incident beam 14 as a collimated beam on to the interferometer. This requires that the light source 13 be displaced from the second focusing lens 26 by a distance equal to the focal length of the lens 26. The lens 26 then focuses the light source as a parallel light beam whose image is superimposed on to the fringe pattern.

The configurable imaging system 25 comprises a beam splitter 30 that directs the light emanating from the fringe pattern 23 and images it using a first imaging lens 31 on to the layered object 11 and transmits the light reflected therefrom through a second imaging lens 32 on to a camera 33.

Preferably the component wavelengths of the broadband light source are focused by the focusing lens 21 so that the fringe pattern includes colored fringes. The fringe pattern may be annular or linear in shape.

In some embodiments, the color of the colored fringes changes as a function of displacement of the object from the focal plane of the imaging system 25 thus allowing quantitative measurement of a location of a point on the object as a function of the color of the fringe pattern at this point.

In some embodiments, the pattern of the colored fringes changes as a function of displacement of the object from the focal plane of the imaging system 25 thus allowing quantitative measurement of a location of a point on the object as a function of the fringe pattern at this point.

In other embodiments, the superimposition of the light source's image and the fringe pattern is undesirable in which case the light source 13 may be configured to direct the incident beam as a non-collimated beam on to the interferometer. The image of the light source is no longer formed of parallel beams and so is not superimposed on to the fringe pattern.

The object 11 may include layers 34a, 34b, 34c etc. one of which e.g. 34a is used as a reference. In this case the measured signal is the light reflected from each point of the object and is the interference of the reflections from all the layers at that point and it is proportional to the autocorrelation function of the object's structure. The object may also be part of an optical device such as an optical device that includes a lens upstream of the object to be measured. One optical device that lends itself to measurement using the invention is the eye wherein the object to be measured may be the retina, cornea, tear film or the intra-ocular lens of the eye. As noted above, optical systems having lens upstream of the object to be measured as, of course, is the case when the retina is to be subjected to OCT have traditionally militated against the use of dual beam OCT which is actually an interferometer, since there is a need for a reference mirror. Since the retina is located in an optical system, the reference arm should include an identical optical system and this cannot be attained in measuring variable biological objects. However, the invention avoids the need for the reference arm since the reference layer may be constituted by one surface in the retina.

To this end, the imaging system 25 may be configured to form together with the lens of the optical device a compound lens having a focal plane on the specific plane of the optical device. Thus, in the case of performing OCT on the retina, the imaging system 25 together with the cornea, tear film and the intra-ocular lens of the eye form a compound lens, whose focus may be adjusted by configuring the imaging system 25 thereby ensuring that the fringe pattern is focused on to the desired object plane of the retina.

Figure 2:
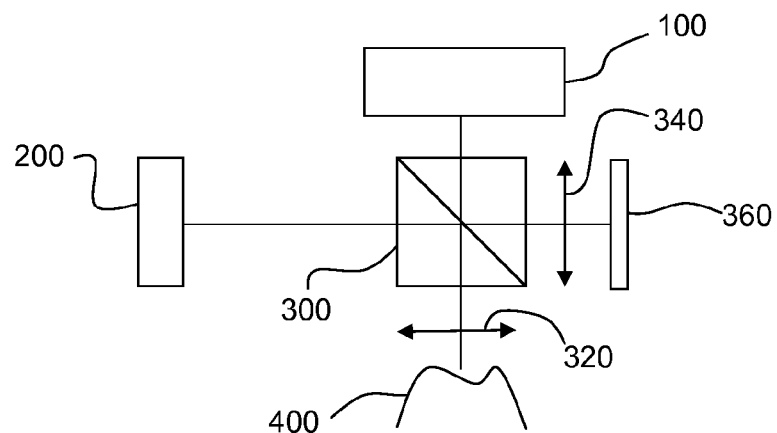
FIG. 2 illustrates an embodiment in which a dual path white light interferometer is combined with a spectral imaging camera or a spectral imager.

As mentioned above, this idea of avoiding the need for reference mirror and enabling measuring the retina in 2D at once rather than point by point, can be implemented using any kind of light source, such as broadband or monochromatic light source, extended or point light source, swept source etc. It can also implemented in point by point Time domain OCT or Fourier domain OCT FIG. 2 shows an embodiment where a dual path white light interferometer such as a Michelson or Linnik interferometer is combined with a spectral imaging camera or a spectral imager to realize a 2D OCT in a FD-OCT type to obtain the surface structure of an object (topography). In the interferometer a fixed reference mirror is used and there is no need for stepping the interferometer's reference mirror. A spectral imaging camera 100 is incorporated with a White light interferometer such as Linnik interferometer 300. In a white light Linnik interferometer, the light incoming from a broadband white light source 200 is split into two beams by a beam splitter 310. One beam is directed through an objective lens 320 to illuminate the object 400 and the other beam is directed to a reference mirror 360 through a lens 340. The light reflected from the object interferes with the light reflected from the mirror on a certain plane where a spectral imaging camera 100 is located. Due to the short coherence length of the white light, fringes are obtained only when the optical path difference between two beams is very small. The cause for this effect is that the different interference of the different wavelengths overlap and the overall result is that the visibility is reduced. When the optical path difference between two beams is very small, the different fringe patterns of the different wavelengths are still in phase and the fringes are still visible. When the mirror is placed such that the fringes are obtained in the focal plane of the objective lens, the focal plane can be found accurately by analyzing the fringe pattern. In TD OCT, moving the objective or the reference mirror causes the fringe pattern to scan the height of the object, and its contours are obtained.

However, according to the present invention, at each point of the object, the intensity that is obtained by the white light interferometry is analyzed by means of a spectral imaging camera. This optical setup has the advantages of both the TD OCT and FD OCT. In this setup there is a static interferometer in the light path inside the optical system and there is no need for stepping the reference mirror as in FD OCT. This interferometer provides the height data through the interference between the light that comes from the object and the light that comes from the reference mirror similarly to the FD OCT. In the regular FD OCT the spectrum of the light is measured using dispersion devices such as grating. Using the spectral data, the optical path differences (translated to the heights in the object) are calculated by Fourier Transform. Since the spectral data occupies one dimension of the detectors array, there is a need for a spatial scan of the object in order to measure a complete 2D object. However in the suggested setup a Hyperspectral Camera is used to measure the 2D spectral data of a 2D object simultaneously thus there is no need for spatial scan.

Figure 3:
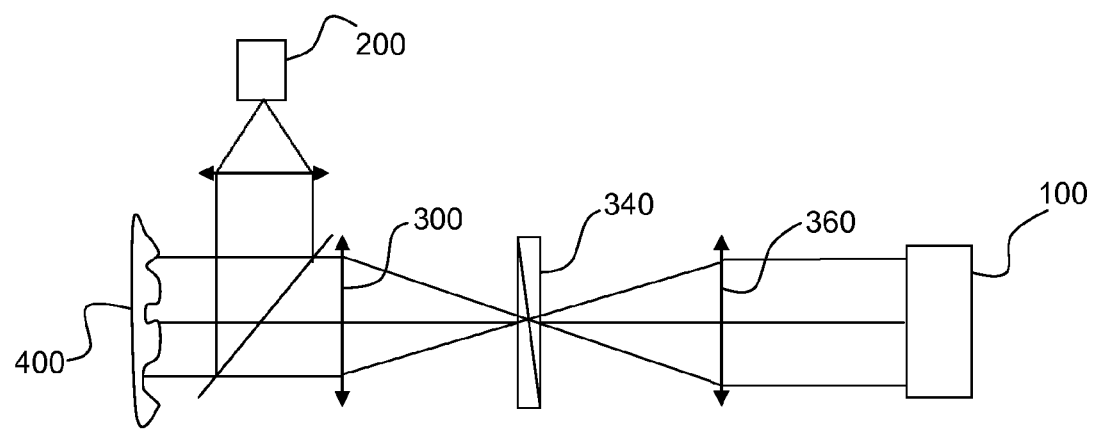
FIG. 3 illustrates a common path interferometer is combined with a spectral imaging camera or a spectral imager.

FIG. 3 illustrates an embodiment in which a common path interferometer such as Zernike phase contrast optical system is combined with a spectral imaging camera or a spectral imager to realize a 2D OCT in a FD-OCT type for topography. In this embodiment a spectral imaging camera 100 is incorporated with a white light common path interferometer. In a common path interferometer based on Zernike phase contrast optical system, the light incoming from a broadband light source 200 illuminates the object 400 which is located at the front focal plane of the lens 300. The reflected light is gathered by the lens 300 and propagates to the back focal plane of the lens 300. It is well known that when a coherent point light source illuminates an object which is located at the front focal plane of a lens, the 2D Fourier transform of the complex transmission or the complex reflection function (in transmission or reflection mode) is obtained in the light source's image plane. In a collimated light illuminating the object the 2D Fourier transform of the complex transmission or the complex reflection function is obtained in the back focal plane of the lens 300. In the back focal plane of the lens 300 there is Diffractive Optical Element (DOE) 340 that delays one part of the wavefront relative to the other part. In general, the phase plate is located in the center of the back focal plane, thus it delays the lower spatial frequencies of the object relative to the higher spatial frequencies by a phase delay $\Delta\Phi=\pi/2$. The second lens 360 creates a successive 2D Fourier transform of said modified wavefront on its back focal plane in which the spectral imaging camera 100 is located. Since the lower spatial frequencies of the object and the higher spatial frequencies interfere, an image of the object is created on the camera where now the phase map of the complex transmission or the complex reflection function of the object modifies the intensity map of the object accordingly. For this kind of interferometer, the lower spatial frequencies part of the wavefront can be considered as a reference beam for the higher spatial frequencies part of the wavefront. Accordingly, as the wavelength is changed the interference pattern at each point of the image will be oscillating between instructive and destructive interference in a similar manner to the dual path interferometer. The main difference is that in the common path interferometer the reference beam is the lower spatial frequencies part of the wavefront which is object dependent. Since each wavelength "sees" different object, the "reference beam" is different for each wavelength, the interference intensity oscillation envelope at each image's point might be modulated relative to the interference intensity oscillation envelope in the dual path interferometer. However, since the change of the "seen" object of close wavelengths is small and continuous it is expected that the main oscillation frequency between instructive and destructive interference is similar to the oscillation frequency in the dual path interferometer. Thus, the common path interferometer also provides the height data through the interference as the FD OCT. In a similar manner, the spectrum of the light can be measured using dispersion devices such as grating in a scanning mode or a Hyperspectral camera in the imaging mode. The optical path differences (translated to the heights in the object) can be calculated by Fourier Transforming the spectral data.

An extension of this idea is when the interference of the common path interferometer is created by shearing the wavefront or part of it relative to itself or relative to other as in shear interferometry. As the wavelength is changed the interference intensity at each point of the image will be oscillating between instructive and destructive interference in a similar manner to the dual path interferometer and the height can be calculated by Fourier transforming the interferogram.

It is to be understood that whenever hereafter a common path interferometer is mentioned it is meant a common path interferometer where the interference is obtained by amplitude division interference or by wavefront division interference.

Figure 4:
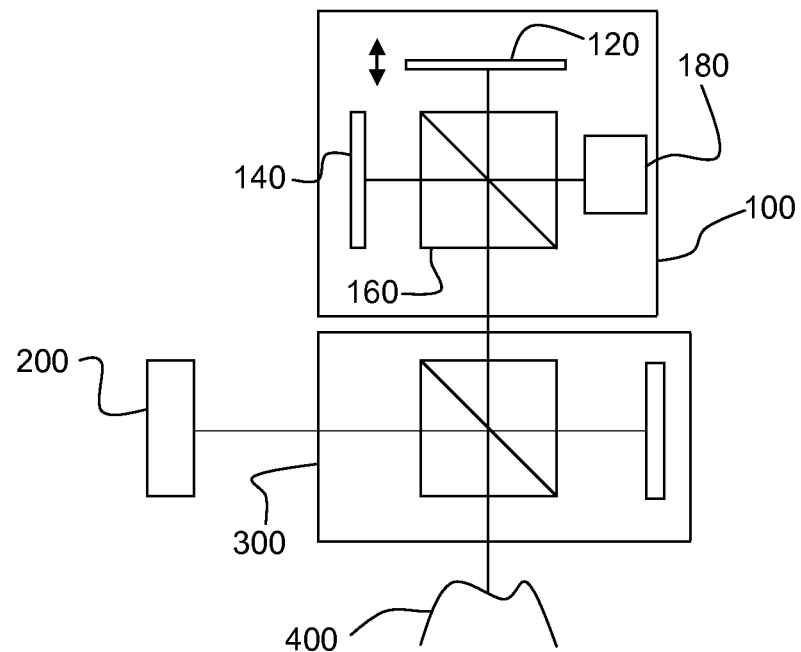
FIG. 4 illustrates a Fourier Transform Hyperspectral Camera that is attached to a static dual path interferometer.

FIG. 4 illustrates another embodiment in which the Hyperspectral Camera 100 attached to a static dual path interferometer 300 is specifically a Fourier Transform Hyperspectral Camera. In this embodiment, a broadband light source 200 illuminates an object 400 through a static dual path interferometer 300. The light that is reflected from the object propagates through the static dual path interferometer 300 to the Hyperspectral Camera 100. The Hyperspectral Camera 100 consists of a beam splitter 160, a moving mirror 120, a static mirror 140 and a camera 180. This optical system is configured as an imaging system that images a point on the object into a pixel in the camera. The Fourier Transform Hyperspectral Camera is actually a camera that is attached to an interferometer. The camera creates the interferogram of each point of the scene which is the intensities of the incoming light from this point at different Optical Path Difference (OPDs) of the interferometer. Fourier transforming (or Cosine Fourier Transforming) the interferogram gives the spectrogram which is the spectrum data of the incoming light from that certain point. However, in FD OCT the height of a certain point in the object is calculated by Fourier transforming the spectrogram of that point obtained by a fixed mirror interferometer. This implies that when a Fourier Transform Hyperspectral Camera is attached to a fixed mirror dual path interferometer, there is no need for performing the Fourier Transform calculations twice—one for the Fourier Transform Hyperspectral Camera to obtain the spectrogram and one for the FD OCT that is realized by the fixed mirror dual path interferometer to obtain the interferogram from the spectogram. The Hyperspectral Camera provides already the required height data without calculations. Whenever the OPD in the interferometer inside the Hyperspectral Camera is equivalent to the OPD between a point on the object and the static reference mirror in the static interferometer object's arm, the signal on the detector is maximal. Actually the signal at the Hyperspectral Camera is the interferogram in which by Fourier transforming it, the spectral data of the incoming light from each point is calculated. This setup is a kind of TD OCT but it releases the requirement for attaching a movable mirror interferometer to the object. In this scheme a fixed mirror interferometer is attached to object and the interferogram is obtained inside the Hyperspectral Camera.

Figure 5:
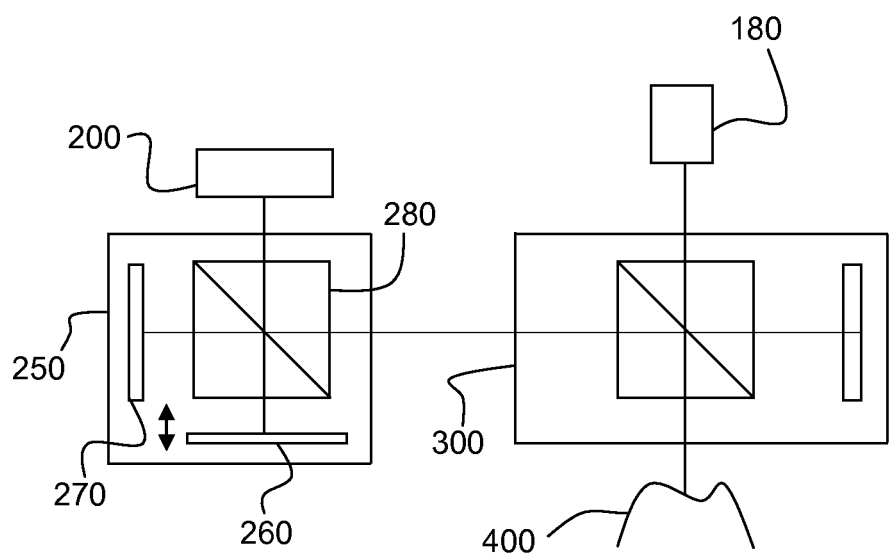
FIG. 5 illustrates a monochrome camera attached to a static dual path interferometer while the object is illuminated by a modulated broadband light source.

FIG. 5 illustrates another embodiment in which a camera 180 is attached to a static dual path interferometer 300 and a broadband light source 200 is modulated by a modulator 250. The modulated light illuminates the object 400 through the static dual path interferometer 300 and the reflected light propagates to the camera 180 through the static dual path interferometer 300.

The Hyperspectral Camera is a camera that is attached to an interferometer. In a Fourier Transform spectrometry inside the Hyperspectral Camera there is an interferometer. The interferometer inside the spectrometer modulates the incoming light differently for different wavelengths due to the destructive and instructive interference. In a Fourier Transform based on Michelson interferometer, the mirror in one arm is moved and the transmitted light intensity at a certain interferometer state is given by:

$$I_o(v) = k_1 I_i(v) + k_2 I_i(v) + 2\sqrt{k_1 k_2 I_i^2(v)} \cos\left(2\pi \frac{v}{c} OPD\right)$$

Where $v$ is the optical frequency, $k_1$ and $k_2$ are the splitting parameters of the interferometer, $I_i(v)$ is the intensity of incoming light in a certain optical frequency and OPD is the Optical Path Difference of the two interferometer's arms.

When, $k_1=k_2=0.5$ the transmitted light intensity is $$I_o(v) = I_i(v)\left[1 + \cos\left(2\pi \frac{v}{c} OPD\right)\right] = \tau(v) I_i(v)$$

where $$\tau(v) = 1 + \cos\left(2\pi \frac{v}{c} OPD\right) = 1 + \cos(2\pi f_{OPD} v)$$

is the spectral transmission function of the interferometer and $$f_{OPD} = \frac{OPD}{c}.$$

The spectrometer serves as a filter with a varying cosine spectral transmission function dependent on its current OPD between its mirrors. However, this filter can be located anywhere in the optical path of the light, and instead of placing the interferometer 250 just before the camera it can be also located just after the light source. In this configuration the spectrum of the incoming light from the light source is modulated with a varying cosine function before impinging on the object by moving its movable mirror 260. The frequency of said varying cosine modulation function that modulated the spectrum is determined by the OPD of the two interferometer's mirrors 260 and 270. This implies that whenever the OPD in the modulating interferometer matches the OPD between the object 400 and the fixed mirror in the fixe interferometer, the signal on the detector is maximal.

This embodiment describes a kind of OCT in which there is no need for using a spectrometer and or moving mirrors in the interferometer as long as the spectrum of a broadband light source can be modulated. Modulating the light source serves as using an interferometer, thus whenever an interferometer is needed, the interferometer can be omitted as long as the light source is spectrally modulated as described above. Accordingly, the Michelson interferometer in FTS can be omitted when the light source is spectrally modulated. The modulating device is not limited to a Michelson interferometer and can be implemented using any kind of spectral modulators such as Babinet compensators, prisms or any interferometric schemes such as a scanning mirror interferometer or a Tunable Fabry-Perot interferometer.

Figure 6:
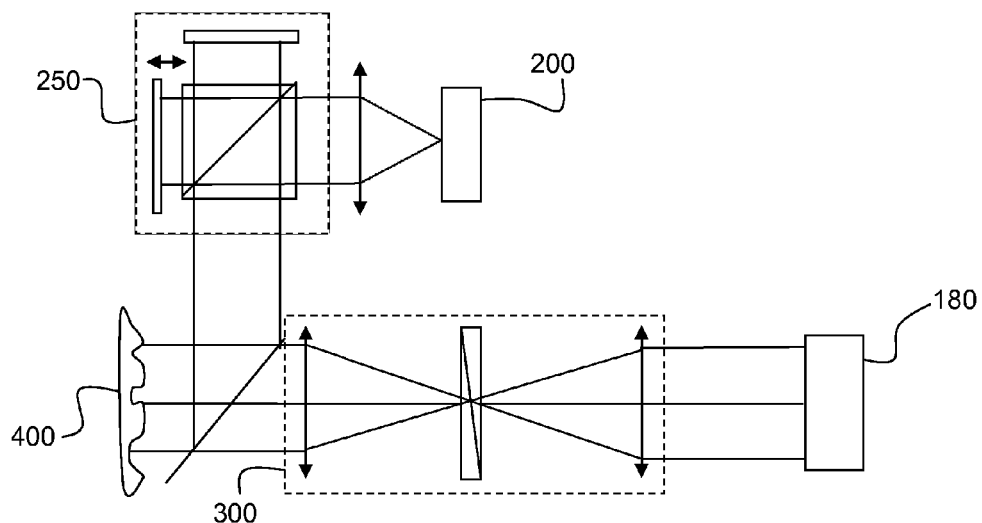
FIG. 6 illustrates a monochrome camera attached to a static common path interferometer while the object is illuminated by a modulated broadband light source.

FIG. 6 illustrates another embodiment in which a camera 180 is attached to a static common path interferometer 300 and a broadband light source 200 is modulated by a modulator 250. The modulated light illuminates the object 400 and the reflected light propagates to the camera 180 through the static dual path interferometer 300. In a common path interferometer, the lower spatial frequencies part of the wavefront is considered as a reference beam for the higher spatial frequencies part of the wavefront. As the wavelength is changed the interference intensity at each point of the image will be oscillate between instructive and destructive interference in a similar manner as in the dual path interferometer. However, since the "reference beam" is different for each wavelength the frequency of the oscillation between the instructive and destructive interference might be modulated. On the other hand, since the change of the "seen" object of close wavelengths is small and continuous it is expected that the main frequency of the oscillation will be similar to the oscillation frequency in the dual path interferometer. Thus, when the light source's spectrum is modulated by a varying cosine modulation function, it is expected that whenever a certain frequency of said varying cosine modulation function of the light source spectrum matches the main oscillation frequency between the instructive and destructive interference in the common path interferometer, the signal on the detector is maximal.

The modulating device can be implemented using any kind of spectral modulators such as Babinet compensators, prisms or any interferometric schemes such as a scanning mirror interferometer or a Tunable Fabry-Perot interferometer.

In still another embodiment according to the present invention a camera is attached to a static common path interferometer and the light source is extended broadband light source with an arbitrary structure is modulated. In a common path interferometer such a Zernike phase contrast system, when a coherent point light source illuminates an object which is located at the front focal plane of a lens, the 2D Fourier transform of the complex transmission or the complex reflection function (in transmission or reflection mode) is obtained in the light source's image plane. In the light source's image plane, the lower spatial frequencies part of the wavefront is delayed relative to the higher spatial frequencies part of the wavefront and at the back focal plane of the second lens both parts interfere to obtain the image. When an extended light source is used, each point of the light source creates a 2D Fourier transform of the object in the light source's image plane and all these 2D Fourier transforms overlaps but they are not coherent. A phase plate with the light source's structure which is not a point that is located in the light source's image plane, delays not only the lower spatial frequencies part of each 2D Fourier transform of the object but also part of the higher spatial frequencies. Both parts of each 2D Fourier transform of the object that are coherent interfere at the back focal plane of the second lens. All the interference patterns created by each point of the light source overlap non-coherently to create the image. However, as the wavelength is changed the interference intensity at each point of the image will be oscillating between instructive and destructive interference in a similar manner. It is expected that the main frequency of the intensity oscillation will be similar to the intensity oscillation frequency of the dual path interferometer. Thus, when the light source's spectrum is modulated by a varying cosine modulation function, the signal on the detector should be maximal whenever a certain frequency of the varying cosine modulation function of the light source's spectrum matches the main intensity oscillation frequency in the common path interferometer.

The structure of the extended light source may be any structure and the structure of the phase plate may be similar or not similar to the structure of the extended light source as long as part of each wavefront representing each 2D Fourier transform of the object is delayed to another part of the wavefront.

The phase plate may be located in any plane in the optical system as long as part of each wavefront created by illumination of each point of the light source is delayed relative to another part of the wavefront.

The modulating device is not restricted to a Michelson interferometer but it can be implemented using any kind of spectral modulators such as Babinet compensators, prisms or any interferometric schemes such as a scanning mirror interferometer or a Tunable Fabry-Perot interferometer.

The spectrum of the reflected light from the object is calculated taking the following considerations into account. When a Fourier Transform Hyperspectral Camera is attached to a fixed interferometer, the camera creates the interferogram of each point of the object and Fourier transforming the interferogram gives the spectrogram which is the spectrum data of the incoming light from that certain point. However, using a common path interferometer instead of using a dual path interferometer, the reflected light from the object may be modulated owing to a non-fixed virtual reference beam and the calculated spectrogram may be incorrect. On the other hand, now that the object structure is measured, the modulation function of the spectrogram can be calculated and the incorrect calculated spectrogram can be repaired.

This idea can be extended to increase the accuracy of the structure measurements. Now that the object structure is measured using the white light interferometry the low pass spatial frequencies of the object as seen by each wavelength can be calculated. These low pass spatial frequencies serve as the reference beam for each wavelength and now it is known. The intensity pattern obtained at each wavelength can be used to calculate the structure of the object more accurately.

Figure 7:
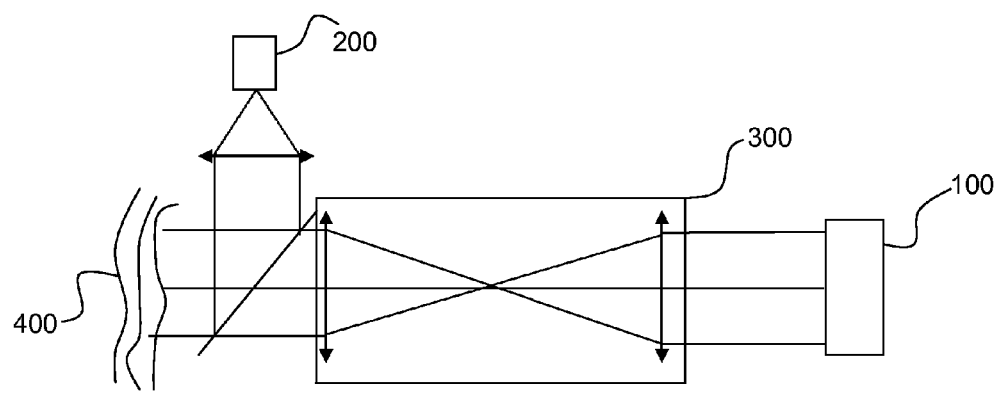
FIG. 7 illustrates a spectral imaging camera or a spectral imager attached to an imaging system without a reference mirror.

FIG. 7 illustrates an embodiment in which a spectral imaging camera or a spectral imager 100 is combined with an imaging system to 300 obtain the layer structure of an object 400 without the need for a reference mirror. An extended broadband light source 200 illuminates the object. In a white light interferometer, the light incoming from a white light source is split into two beams by a beam splitter. As mentioned above, in a conventional dual-path interferometer one beam is directed to the object and the other beam is directed to a reference mirror. The light reflected from the object interferes with the light reflected from the mirror. Actually, the mirror creates an image of the light source that is used as a reference light source and it interferes with the other light sources images that created by the different layers of the object.

The present invention avoids the requirement for a reference mirror for applications where the thicknesses of the different layers are of importance and not the actual topometry. Thus, in such an embodiment, one of the images of the light source created by the different layers can be used as the reference light source for the other images. The imaging system gathers the light reflected light from the different layers at each point of the object into a conjugate point in the detectors array to obtain the interference between the light that is reflected from said different layers at each point of the object. At each image's point, the interference obtained is similar to the interference that is obtained when a reference mirror is used except that in this setup one of the layers is used as reference mirror for the other layers instead of using an additional reference mirror. The intensity function is an autocorrelation function but when one layer has higher reflection coefficient it can serve as a reference. Thus, the interference can be analyzed to obtain the thicknesses of the different layers in the same manner as is analyzed in a white light interferometry by means of a spectral imaging camera that is attached to the imaging optical system as described above.

Figure 8:
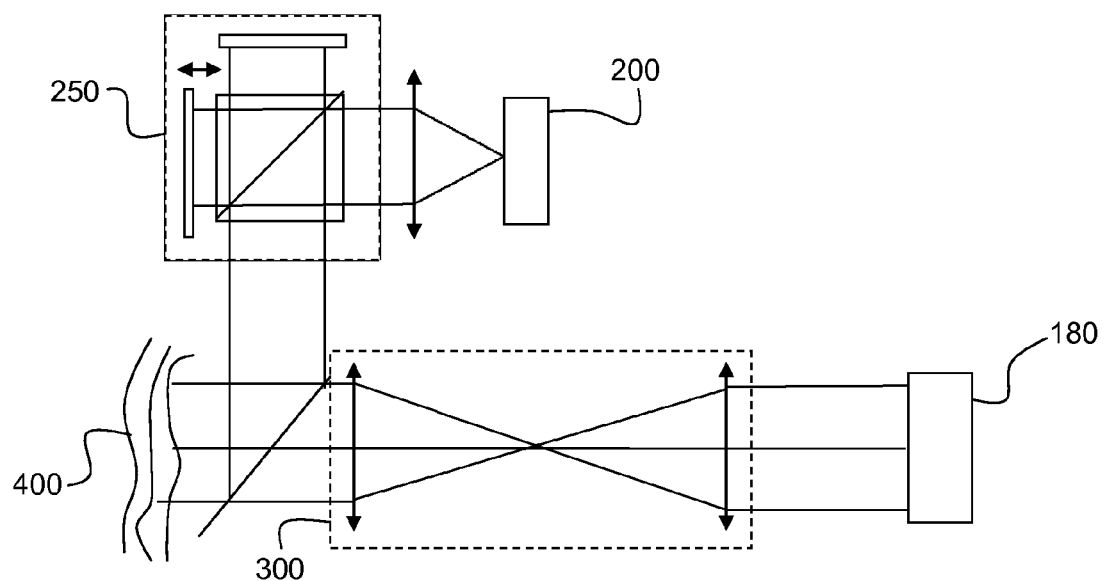
FIG. 8 illustrates a monochrome camera attached to an imaging system while the object is illuminated by a modulated broadband light source.

FIG. 8 illustrates another embodiment according to the present invention in which a camera 180 is attached to an imaging system 300 and where an extended broadband light source 200 is modulated by a modulator 250. The modulated light illuminates a layered object 400. As described above, a spectrally modulated light source serves as using an interferometer in a FTS, and the interferometer can be omitted as long as the light source is spectrally modulated as described above and thus, the Michelson interferometer in FTS can be omitted when the light source is spectrally modulated. For some applications where the thicknesses of the different layers are of importance and not the actual topometry, one layer of the object can be used as the reference for the other layers in the object. The imaging system gathers the light reflected from the different layers at each point of the object into an image point in the detectors array. The reflected light from the different layers at each point of the object interfere to obtain the resulting intensity in that image point. At each image's point, the interference obtained is similar to the interference that is obtained when a reference mirror is used except that in this setup one of the layers is used as the reference for the other layers instead of using an additional reference mirror. Thus, the interference can be analyzed to obtain the thicknesses of the different layers in the same manner as described above. The 2D spectral analysis can be done by means of a spectral imaging camera that is attached to the imaging optical system as described above. However, as described in previous embodiments, when the light source is spectrally modulated, the spectral imaging camera can be replaced by a monochromatic camera.

There are several advantages when no reference mirror is used over the case when a reference mirror is used; The optical setup is much simpler; since no reference mirror is needed a regular optical system for imaging can also be used for measuring the layers thicknesses of the object and its spectral characteristics by only replacing its light source with a modulated light source; in some cases, the ratio between the signals to the background light is higher than in the case when a reference mirror is used since the light reflected from the reference mirror is also added to the background light.

A priori knowledge of the spectral characteristics of the different layers of the object can be used to analyze the signal in different wavelength bands. By comparing the signals that would be obtained in different wavelength bands, some ambiguities in interpreting the results can be removed.

The invention claimed is:

1. A system for performing dual path, two-dimensional Optical Coherence Tomography (OCT) on an object having a plurality of layers, and lying in a specific plane, said system comprising:
an extended broadband light source for producing an incident light beam,
an interferometer that comprises a beam splitter and that is configured to intercept the incident light beam and direct the incident light beam via the beam splitter such that the beam splitter splits the incident light beam into first and second component beams and creates an optical path difference between the first component beam and a reflection of the second component beam;
a focusing lens having a focal plane and that is configured to focus the first component beam and the reflection of the second component beam to form a fringe pattern on the focal plane of the focusing lens;
a configurable imaging system configured to image the fringe pattern on to said specific plane in which the object lies; and
a detector array configured to gather light that is reflected from respective points of the object into respective, conjugate points in the detector array,
such that an intensity of the gathered light at a given conjugate point in the detector array is obtained by interference between light reflected from the layers of the object at the corresponding point of the object.

2. The system according to claim 1, wherein the focusing lens is configured to form the fringe pattern by forming a fringe pattern that has colored fringes.

3. The system according to claim 2, wherein the focusing lens is configured to form the fringe pattern by forming a fringe pattern that has color fringes, colors of the colored fringes changing as a function of displacement of the object from the focal plane of the focusing lens thus allowing quantitative measurement of a location of a point on the object as a function of the color of the fringe pattern at said point.

4. The system according to claim 2, wherein the focusing lens is configured to form the fringe pattern by forming a fringe pattern that has color fringes, a pattern of the colored fringes changing as a function of displacement of the object from the focal plane of the focusing lens thus allowing quantitative measurement of a location of a point on the object as a function of the fringe pattern at said point.

5. The system according to claim 1, wherein the focusing lens is configured to form the fringe pattern by forming a fringe pattern that is annular.

6. The system according to claim 1, further including a second focusing lens between the light source and the interferometer and being located relative to the light source so as to direct the incident light beam as a collimated beam on to the interferometer whereby an image of the light source is superimposed on to the fringe pattern.

7. The system according to claim 1, wherein the light source is configured to direct the incident light beam as a non-collimated beam on to the interferometer whereby an image of the light source is not superimposed on to the fringe pattern.

8. The system according to claim 1, wherein the light source comprises a swept source.

9. The system according to claim 1, wherein the object includes an object that is part of an optical device that includes a lens, and wherein the configurable imaging system is configured to form a compound lens together with the lens of the optical device, the compound lens having a focal plane that lies on the specific plane in which the object lies.

10. The system according to claim 9, wherein the optical device is an eye that includes an intra-ocular lens, and wherein the configurable imaging system is configured to form a compound lens together with the intra-ocular lens of the eye, the compound lens having a focal plane that lies on the specific plane in which the object lies.

11. The system according to claim 10, wherein the object is a retina of the eye, and wherein the configurable imaging system is configured to form a compound lens together with the intra-ocular lens of the eye, the compound lens having a focal plane that lies on a specific plane in which the retina lies.

12. The system according to claim 10, wherein the object is the intra-ocular lens of the eye, and wherein the configurable imaging system is configured to form a compound lens together with the intra-ocular lens of the eye, the compound lens having a focal plane that lies on a specific plane in which the intra-ocular lens lies.

13. The system according to claim 1, wherein the object is a cornea of the eye, and wherein the configurable imaging system is configured to image the fringe pattern on to a specific plane in which the cornea lies.

14. The system according to claim 1, wherein the object is a tear film of the eye, and wherein the configurable imaging system is configured to image the fringe pattern on to a specific plane in which the tear film lies.

15. The system according to claim 1, wherein the detector array comprises a spectral imager.

16. The system according to claim 1, wherein the spectral imaging device comprises a hyperspectral camera.

17. The system according to claim 1, further comprising a spatial light modulator that is configured to modulate a spectrum of the light source over time, such that the fringe pattern that is focused on to the specific plane in which the object lies varies with time.

18. The system according to claim 1, wherein the spatial light modulator comprises an interferometric system that includes a movable mirror, and wherein the spatial light modulator is configured to modulate the spectrum of the light source over time by moving the movable mirror of the interferometric system.

* * * * *